US00PP21364P2

(12) United States Plant Patent
Stahlhut

(10) Patent No.: US PP21,364 P2
(45) Date of Patent: Oct. 5, 2010

(54) CARNATION PLANT NAMED 'CFPC PINK TESS'

(50) Latin Name: *Dianthus caryophyllus*
Varietal Denomination: CFPC Pink Tess

(75) Inventor: Roy Stahlhut, Watsonville, CA (US)

(73) Assignee: California Florida Plant Company, Salinas, CA (US)

( * ) Notice: Subject to any disclaimer, the term of this patent is extended or adjusted under 35 U.S.C. 154(b) by 0 days.

(21) Appl. No.: 12/459,936

(22) Filed: Jul. 9, 2009

(51) Int. Cl.
*A01H 5/00* (2006.01)

(52) U.S. Cl. ..... Plt./277

(58) Field of Classification Search ..... Plt./277
See application file for complete search history.

(56) References Cited

U.S. PATENT DOCUMENTS

PP16,625 P3 6/2006 Hasegawa ..... Plt./273
PP17,157 P2 10/2006 Hasegawa ..... Plt./273

*Primary Examiner*—Kent L Bell
(74) *Attorney, Agent, or Firm*—Phase M, LLP

(57) ABSTRACT

A new variety of carnation plant named 'CFPC Pink Tess', having a compact form of plant with purple pink flowers.

1 Drawing Sheet

Latin name of the genus and species: Botanical classification: *Dianthus caryophyllus.*

Variety denomination: The new carnation variety denomination is 'CFPC Pink Tess'.

BACKGROUND OF THE INVENTION

The present invention comprises a new and distinct cultivar of hybrid carnation botanically known as *Dianthus caryophyllus*, and referred to by the cultivar name 'CFPC Pink Tess'. The new variety, identified as selection No. 050143, was discovered as a naturally occurring whole plant mutation in a controlled cultivated planting of the variety 'CFPC Tess' (U.S. Plant Pat. No. 16,625), in Salinas, Calif. The new variety 'CFPC Pink Tess' has been asexually reproduced by vegetative side shoot cuttings in Salinas, Calif. and the distinguishing characteristics are retained through successive generations of asexual reproduction.

BRIEF SUMMARY OF THE INVENTION

'CFPC Pink Tess' is a potted spray-type carnation plant variety having a compact form of plant with well presented flowers with nice purple pink color.

COMPARISON WITH ORIGINAL VARIETY

Plants of the new carnation variety 'CFPC Pink Tess' are similar to the original variety 'CFPC Tess' in plant habit and growth rate. Under similar growing conditions in Salinas, Calif., under commercial practice, plants of the new carnation variety 'CFPC Pink Tess' differed from plants of the original variety 'CFPC Tess' in the following characteristic:

1. The new variety 'CFPC Pink Tess' produces purple-pink flowers whereas the original variety 'CFPC Tess' produces purple flowers.

COMPARISON WITH OTHER SIMILAR VARIETIES

Plants of the new carnation variety 'CFPC Pink Tess' are similar to plants of the variety 'CFPC Lipstick' (U.S. Plant Pat. No. 17,157) in plant habitat and growth rate. Under similar growing conditions, however, in Salinas, Calif., under commercial practice, plants of the new carnation variety 'CFPC Pink Tess' differed from plants of 'CFPC Lipstick' in the following characteristics:

1. The flowers of the new variety 'CFPC Pink Tess' are lighter pink color than flowers of the variety 'CFPC Lipstick'.
2. The plants of the new variety 'CFPC Pink Tess' are taller than plants of the variety 'CFPC Lipstick'.

BRIEF DESCRIPTION OF ILLUSTRATION

A typical specimen of the plant and flowers for the new carnation variety 'CFPC Pink Tess' is shown in the accompanying photograph. The colors shown are as true as possible within the usual limits of this kind of illustration. FIG. 1 is a whole plant view of the new variety 'CFPC Pink Tess' grown in a pot. The plant shown in the illustration is 120 days from date of planting.

DETAILED BOTANICAL DESCRIPTION

The following description of the new carnation variety 'CFPC Pink Tess' is of plants 120 days from planting grown in a commercial greenhouse in Salinas, Calif. The cultivar has not been observed under all possible environmental conditions. The phenotype may vary significantly with variations in the environment such as temperature, length of day and light intensity without any variance in genotype.

Plants of the new variety have been grown successfully under temperature conditions averaging about 18° C. at night and about 24° C. to 28° C. during the day under light conditions of about 12 hours. Plants are daylight neutral and flower throughout the year. Chemical growth regulators are not required for production. The new variety may be produced as a potted spray-type carnation. To produce a commercial product the plants may be pinched once with the center bud removed. Pinched plants are about 6 inches tall and about 6 inches in diameter. Flower diameter averages about 2 inches with a crown of about 1 inch. Foliage is generally about 3½ inches long and about ⅜ inch at the widest point. The typical container size for commercial growth is 4½ inches.

It has been observed that the shelf life of the new variety is about 21 days with a time to first bud opening of about 15-16 weeks. The plant hardiness zone has not been determined The commercial classification of the new variety is a potted spray-type. The following description is with respect to a plant produced as a potted spray-type carnation. The plant and flower measurements and foliage size are established as an average using standard commercial cultural practices. In the description of this new variety, color values have been taken from The Royal Horticultural Society Colour Chart (R.H.S.C.C.).

PLANT

Height (inches): 8½.
Form: Herbaceous.
Growing habit: Semi upright.
Branching characteristics: 3-4 laterals per stem.
Breaking action: 6-8 breaks per plant with strong straight stems.
First appearance of color in buds: 101 days after planting.
Vigor: Excellent.
Shelf life: 21 days.
Blooming habit: Spray type.
Blooming season: Year round.
Lastingness of blooms: About 10 days.
Disease (Susceptibility/Resistance observed): Excellent resistance to soil-borne diseases such as *Fusarium oxysporum* and *F. graminearium*, and root rots such as damping off, water molds and similar types, as are typical of carnations.
Pest susceptibility/resistance: Not evaluated or observed.
Drought and temperature susceptibility/resistance: Not evaluated or observed.
Mutation prone: No.
Propagation:
*Type.*—Side shoot cuttings.
*Time to rooting.*—18 days with soil temperatures of about 18° C. to 21° C.
*Rooting habit.*—Good fibrous system.
Growth treatments or special conditions: Single pinch.

FOLIAGE

Stem:
*Length* (*inches*).—7.
*Diameter* (*inches*).—⅜ (at base).
*Texture.*—smooth.
*Cross section.*—Edged.
*Color.*—137A internode. 145C node.
Number of leaves per lateral branch: 14.
Arrangement of leaves: Bi-lateral along the stem.
*Shape of leaf.*—Long, narrow, . lanceolate.
*Size of leaf.*—Width (inches): ⅜ . Length (inches): 3½.
*Leaf Apex.*—Acute.
*Edge.*—Smooth.
*Base.*—Smooth.
*Aspect.*—Elliptic.
*Surface texture.*—Top: Smooth. Bottom: Smooth.
Leaf venation: Prominent mid-vein at underside.
Leaf longitudinal axis: Recurved.
Leaf cross section (upper side): Weakly concave.
Leaf color: Mature Leaf, upper side: 137A; under side: 137B.
*Young leaf, upper side.*—139A; under side: 137A.
Leaf waxy layer: Medium.

FLOWER

Flower appearance: Matte to shiny.
Flower type: Double.
Flower profile of upper part of corolla: Convex.
Flower profile of lower part of corolla: Concave.
Flower shape: Somewhat dome shape rounded.
Number of blossom per branch: 5-6.
*Depth of fully expanded blossoms* (*inches*).—1.
*Diameter of fully expanded blossoms* (*inches*).—2.
Calyx:
*Sepals number.*—5.
*Length* (*inches*).—1⅛.
*Width* (*inches*).—½.
*Color.*—Outer side base: 144B. Outer side middle to tip: 144A. Inner side: 138A.
*Texture.*—Smooth.
*Appearance.*—Matte with waxy bloom.
*Shape.*—Cylindrical.
Flower petals:
*Form/shape.*—Fan shape.
*Petal edge.*—Edge type: crenate-dentate. Width (inches): 1/16 . Depth (inches): 1/16.
*Texture.*—Smooth.
*Appearance.*—Matte-shiny.
*Petal surface of blade.*—Undulating.
*Number per flower.*—28.
*Outer petals.*—Length (inches): 1½ . Width (inches): 1.
*Inner petals.*—Length (inches): 1⅜ . Width (inches): ¾.
Fragrance: Absent.
Flower bud (at onset of color):
*Length* (*inches*).—1¼.
*Diameter* (*inches*).—½.
*Form/shape.*—Cylindrical.
Flower color:
1. *General tonality.*—Purple pink.
2. *Petals, upper surface.*—62A.
3. *Petals, lower surface.*—62D.
4. *Petals, edge.*—62A.
5. *Petals, center.*—62D.
6. *Early bud.*—62A.
Petal macule (random spots): Absent.
Flower progression with age: Color slightly fades to lighter color.

REPRODUCTIVE ORGANS

Gynoecium: Pistillate:
*Pistil number.*—1.
*Pistil length* (*inches*).—1½.
*Stigma color.*—White or cream.
*Stigma shape.*—Filamentous.
*Style color.*—Whiter than 155D.
*Style length* (*inches*).—1¼.
*Style number.*—Only three.
Ovary:
*Shape.*—Ovoid.
*Surface.*—Smooth.
*Color:.*—Base: 145C. Body: 145C. Apex: 145A.
Androecium: None produced.
Fruit and seeds: None produced.

What is claim is:

1. A new and distinct variety of carnation plant, substantially as described and illustrated herein.

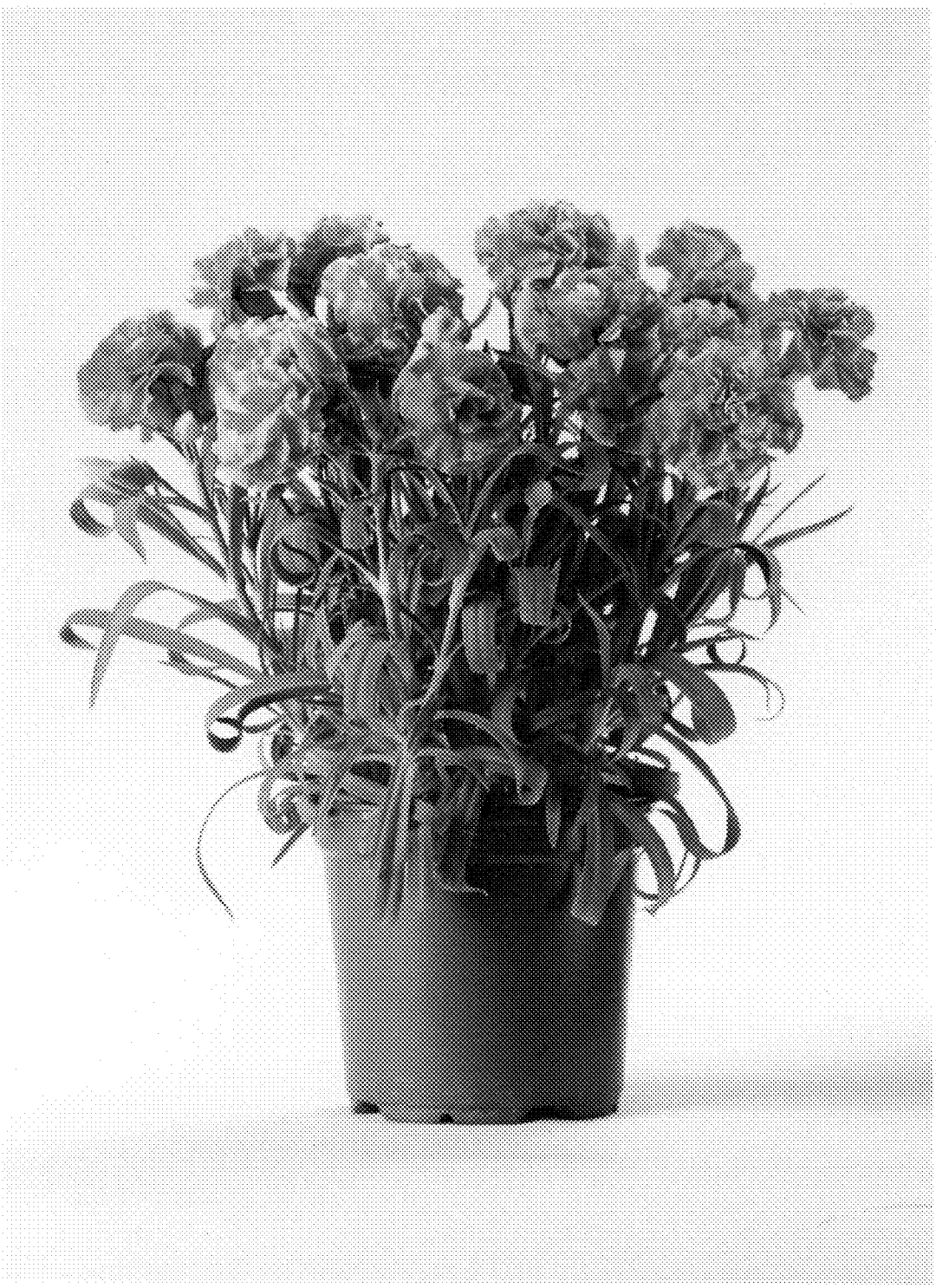

* * * * *